United States Patent [19]
Verbeek

[11] Patent Number: 6,071,287
[45] Date of Patent: Jun. 6, 2000

[54] INTRODUCER FOR SINGLE OPERATOR STENT DELIVERY SYSTEM

[75] Inventor: Marcel A. E. Verbeek, Heerlen, Netherlands

[73] Assignee: Medtronic, Inc., Minneapolis, Minn.

[21] Appl. No.: 09/220,807

[22] Filed: Dec. 23, 1998

[51] Int. Cl.[7] ................................................. A61M 25/01
[52] U.S. Cl. ............................................ 606/108; 604/96
[58] Field of Search .................................. 606/108, 194; 604/96, 171, 264

[56] References Cited

U.S. PATENT DOCUMENTS

| | | | |
|---|---|---|---|
| 3,382,872 | 5/1968 | Rubin | 128/214.4 |
| 3,467,101 | 9/1969 | Fogarty et al. | 606/194 |
| 3,677,244 | 7/1972 | Hassinger | 128/124.4 |
| 3,877,429 | 4/1975 | Rasumoff | 128/214.4 |
| 4,166,469 | 9/1979 | Littleford | 128/784 |
| 4,243,050 | 1/1981 | Littleford | 128/784 |
| 4,306,562 | 12/1981 | Osborne | 128/348 |
| 4,345,606 | 8/1982 | Littleford | 128/784 |
| 4,699,611 | 10/1987 | Bowden | 604/51 |
| 5,382,230 | 1/1995 | Bonn | 604/32 |
| 5,415,664 | 5/1995 | Pinchuk | 606/108 |
| 5,424,771 | 6/1995 | Imran | 604/281 |
| 5,456,694 | 10/1995 | Marin et al. | 606/198 |
| 5,458,615 | 10/1995 | Klemm et al. | 606/198 |
| 5,601,568 | 2/1997 | Chevillon et al. | 606/108 |
| 5,643,296 | 7/1997 | Hundertmark et al. | 606/159 |
| 5,690,644 | 11/1997 | Yurek et al. | 606/108 |
| 5,707,376 | 1/1998 | Kavteladze et al. | 606/108 |
| 5,776,140 | 7/1998 | Cottone | 606/108 |
| 5,944,695 | 8/1999 | Johnson et al. | 604/164 |
| 5,951,568 | 9/1999 | Schatz | 606/108 |
| 5,971,991 | 10/1999 | Sunderland | 606/108 |

FOREIGN PATENT DOCUMENTS

| | | | |
|---|---|---|---|
| 0 606 164 A1 | 1/1994 | European Pat. Off. | A61M 25/01 |
| 0 686 379 A2 | 6/1995 | European Pat. Off. | A61F 2/06 |
| 0 686 379A3 | 3/1996 | European Pat. Off. | A61F 2/06 |
| WO 95/21592 | 8/1995 | WIPO | A61F 2/06 |
| WO 95/28976 | 11/1995 | WIPO | A61M 5/00 |

*Primary Examiner*—Paul J. Hirsch
*Assistant Examiner*—Michael B. Priddy

[57] ABSTRACT

A method and apparatus are disclosed for introducing stents into intravascular guiding catheters. The introducer includes clamps to retain the introducer in a desired position on the stent delivery catheter prior to deployment, as well as a tubular body extending from the clamp that preferably protects the distal end of the stent delivery catheter prior to deployment. The clamp is movable to selectively clamp or release the shaft of the stent delivery catheter. In addition, the clamp includes a guidewire channel that clamps the guidewire in a fixed position relative to the clamp while simultaneously releasing the shaft of the stent delivery catheter to allow the stent to be advanced over the guidewire. These operations can preferably be accomplished by a single operator.

17 Claims, 6 Drawing Sheets

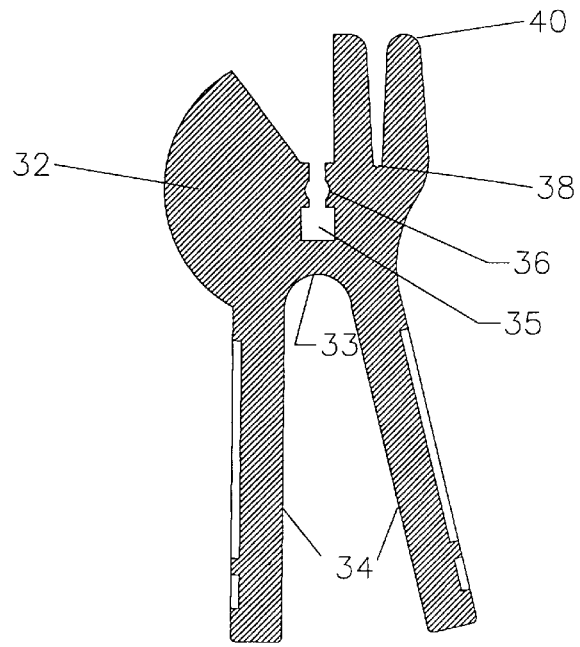
FIG. 7
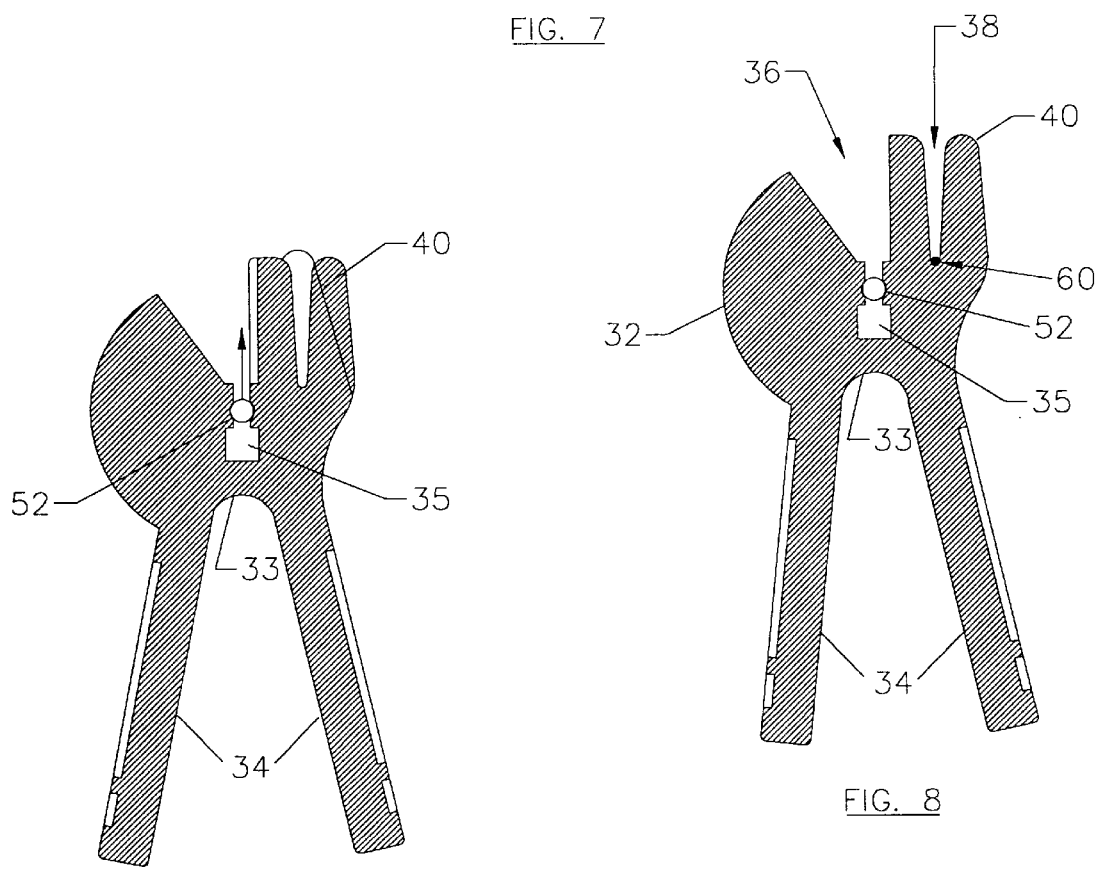
FIG. 8
FIG. 9

INTRODUCER FOR SINGLE OPERATOR STENT DELIVERY SYSTEM

FIELD OF THE INVENTION

The present invention relates to devices and methods for introducing intravascular stent implants on delivery devices. More particularly, the present invention relates to devices and methods for introducing intravascular stent implants on delivery devices.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system near to the site of therapy. A guiding catheter, for example, can then be advanced over the first guidewire to a point just proximal of the stenosis. The guiding catheter typically terminates in a device outside of the patient that includes one or more ports for the introduction of other devices. One common device is typically referred to as a Y-connector.

After the guiding catheter is in position, the first guidewire is often removed. A balloon catheter on a smaller diameter second guidewire is then advanced within the guiding catheter to a point just proximal of the stenosis. The second guidewire is advanced into the stenosis, followed by the balloon on the distal end of the catheter. The balloon is inflated causing the site of the stenosis to widen.

Dilatation of the occlusion with a balloon can, however, form flaps, fissures and dissections which threaten reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. Stents may measurably decrease the incidence of restenosis after angioplasty thereby reducing the likelihood that a secondary angioplasty procedure or a surgical bypass operation will be necessary.

A stent can be delivered as part of the dilatation procedure (with the stent mounted over the balloon). Alternatively, the stents can be delivered by yet another catheter inserted through the guiding catheter after the balloon catheter has been removed. This stent delivery catheter is typically inserted over the second guidewire used to guide the balloon into the stenotic region through the guiding catheter.

Among the problems facing those attempting to advance stent delivery catheters is the need to maintain the proper axial positions of the second guidewire relative to the stenotic region and also advance the stent delivery catheter over the second guidewire. In many cases, two people may be required to introduce the stent delivery catheter into the guiding catheter over the second guidewire, as well as advance the stent delivery catheter over the second guidewire to position the stent in the stenotic region for deployment.

Another problem associated with some introducers is that they are mounted on the stent delivery catheters by the user which typically requires the stent to be inserted through at least a portion of the introducer. That action may damage the stent or dislodge it from its proper mounting location on the stent delivery catheter.

SUMMARY OF THE INVENTION

The present invention provides devices and methods for introducing stents into intravascular guiding catheters. The introducers include clamps to retain the introducer in a desired position on the stent delivery catheter prior to deployment, as well as a tubular body extending from the clamp that preferably protects the distal end of the stent delivery catheter prior to deployment. The clamp is movable to selectively clamp or release the shaft of the stent delivery catheter. In addition, the clamp includes a guidewire channel that clamps the guidewire in a fixed position relative to the clamp while simultaneously releasing the shaft of the stent delivery catheter to allow the stent to be advanced over the guidewire. These operations can preferably be accomplished by a single operator.

In one aspect, the present invention provides an introducer for introducing a catheter into a stent delivery system, the introducer including a generally tubular body having a proximal end and a distal end, the body including a lumen formed by a sidewall and an opening in the sidewall between the proximal and distal ends; a clamp attached to the proximal end of the body, the clamp including a catheter shaft channel in coaxial alignment with the tubular body lumen, the catheter shaft channel movable between a clamping width and an advancing width that is larger than the clamping width; and a guidewire channel offset from the catheter shaft channel, the guidewire channel capable of receiving and retaining a guidewire in a fixed position relative to the clamp.

In other aspects, the introducers may include one or more of the following features or characteristics: a catheter shaft channel biased in the clamping width; a movable clamp member located on one side of the catheter shaft channel; a movable clamp member located on one side of the catheter shaft channel with the guidewire channel located in the movable clamp member; a movable clamp member that rotates about an axis of rotation when the catheter shaft channel is moved from the clamping width to the advancing width; a first lever operatively attached to a movable clamp member and a second lever fixedly attached to the clamp, whereby rotation of the first lever rotates the movable clamp member about the axis of rotation; a catheter shaft channel axis defined by the catheter shaft channel and a guidewire channel axis defined by the guidewire channel, wherein the catheter shaft channel axis and the guidewire channel axis are offset from and generally aligned with each other; and a length between the opening and the distal end in the lumen of the tubular body that is sufficient to receive a stent therein.

In another aspect, the present invention provides an introducer for introducing a catheter into a stent delivery system, the introducer including a generally tubular body having a proximal end and a distal end, the body including a lumen formed by a sidewall and an opening in the sidewall between the proximal and distal ends; a clamp attached to the proximal end of the body, the clamp including a movable clamp member located on one side of a catheter shaft channel that is in coaxial alignment with the lumen of the tubular body, wherein the movable clamp member rotates about an axis of rotation to move the catheter shaft channel from a clamping width to an advancing width that is larger than the clamping width, and further wherein the movable clamp member is biased to maintain the catheter shaft channel in the clamping width; and a guidewire channel offset from the catheter shaft channel, the guidewire channel capable of receiving and retaining a guidewire in a fixed position relative to the clamp.

In another aspect the present invention provides a combination including a catheter having a shaft with proximal and distal ends; a stent located proximate the distal end of the shaft of the catheter; an introducer including a generally tubular body having a proximal end and a distal end, the body including a lumen formed by a sidewall and an opening in the sidewall between the proximal and distal ends; wherein the stent and a portion of the shaft of the catheter are located within the lumen between the opening and the distal end of the tubular body; a clamp attached to the proximal end of the body, the clamp including a catheter shaft channel in coaxial alignment with the tubular body lumen, the catheter shaft channel movable between a clamping width and an advancing width that is larger than the clamping width, wherein the shaft of the catheter is located within the catheter shaft channel; and a guidewire channel offset from the catheter shaft channel, the guidewire channel capable of receiving and retaining a guidewire in a fixed position relative to the clamp.

In another aspect, the present invention provides a method of introducing a stent in a catheter based stent delivery system by providing a combination of a catheter having a shaft with a proximal end, a distal end and a guidewire lumen; a stent located proximate the distal end of the shaft of the catheter; and an introducer including a generally tubular body having a proximal end and a distal end, the body including a lumen formed by a sidewall and an opening in the sidewall between the proximal and distal ends; wherein the stent and a portion of the shaft of the catheter are located within the lumen between the opening and the distal end of the tubular body; a clamp attached to the proximal end of the body, the clamp comprising a catheter shaft channel in coaxial alignment with the tubular body lumen, wherein the shaft of the catheter is located within the catheter shaft channel; and a guidewire channel offset from the catheter shaft channel; inserting a guidewire into the guidewire lumen of the catheter, the guidewire passing into the distal end of the tubular body of the introducer and through the opening in the sidewall of the tubular body; advancing the distal end of the tubular body of the introducer along the guidewire to a guiding catheter; simultaneously increasing the width of the catheter shaft channel from a clamping width to an advancing width and retaining the guidewire within the guidewire channel; and advancing the catheter relative to the guidewire while maintaining the catheter shaft channel at the advancing width.

These and other features and advantages of the present invention are discussed below with respect to various illustrative embodiments of the invention.

BRIEF DESCRIPTION OF THE DRAWINGS

FIG. 7 is a cross-sectional view of the clamp taken along line 7—7 in FIG. 3;

FIG. 8 is a cross-sectional view of the clamp similar to the view of FIG. 7, but with a stent delivery catheter located within the catheter channel and a guidewire located within the guidewire channel;

FIG. 9 is a cross-sectional view of the clamp similar to the view of FIG. 7, but with a stent delivery catheter being removed from the catheter channel;

DETAILED DESCRIPTION OF ILLUSTRATIVE EMBODIMENTS

The present invention provides an introducer useful for introducing stent delivery catheters into, e.g., guiding catheters and for assisting in advancement of the stent delivery catheter over a guidewire already in place within the guiding catheter.

Figure 1:
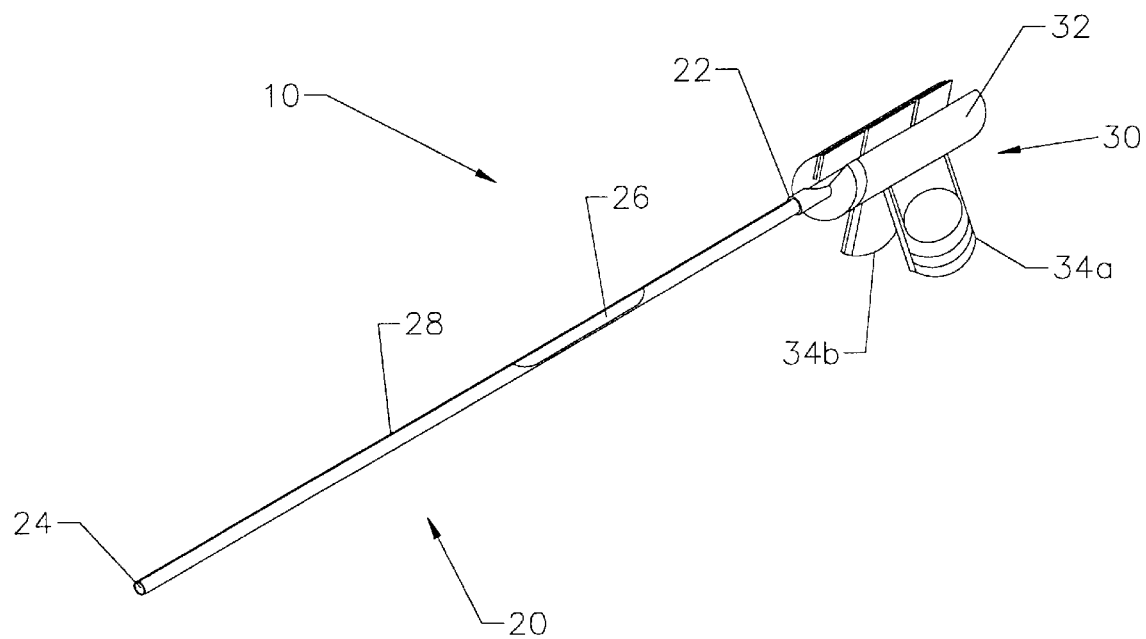
FIG. 1 is a perspective view of one introducer according to the present invention.
Figure 2:
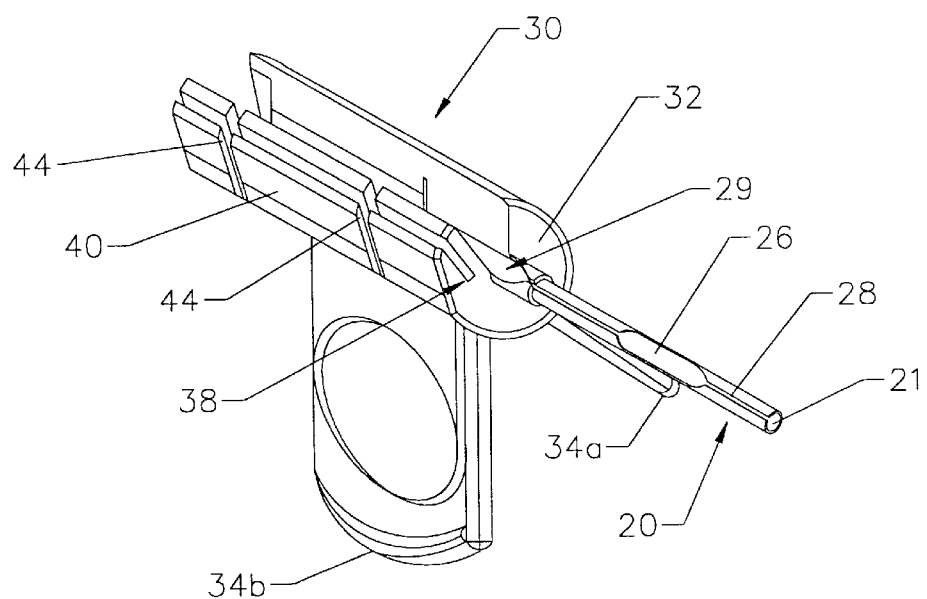
FIG. 2 is an enlarged perspective view of the clamp portion of the introducer of FIG. 1.
Figure 3:
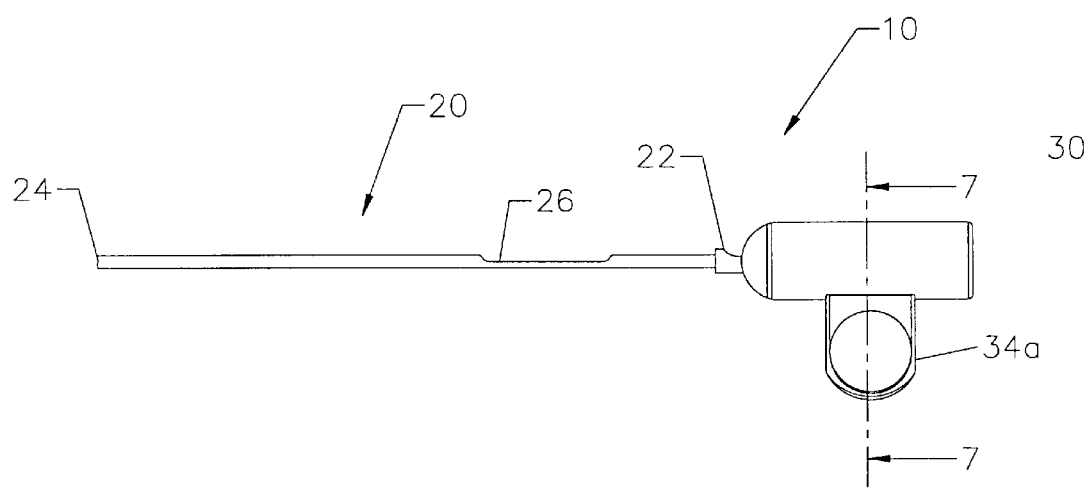
FIG. 3 is a side elevation of the introducer of FIG. 1.
Figure 4:
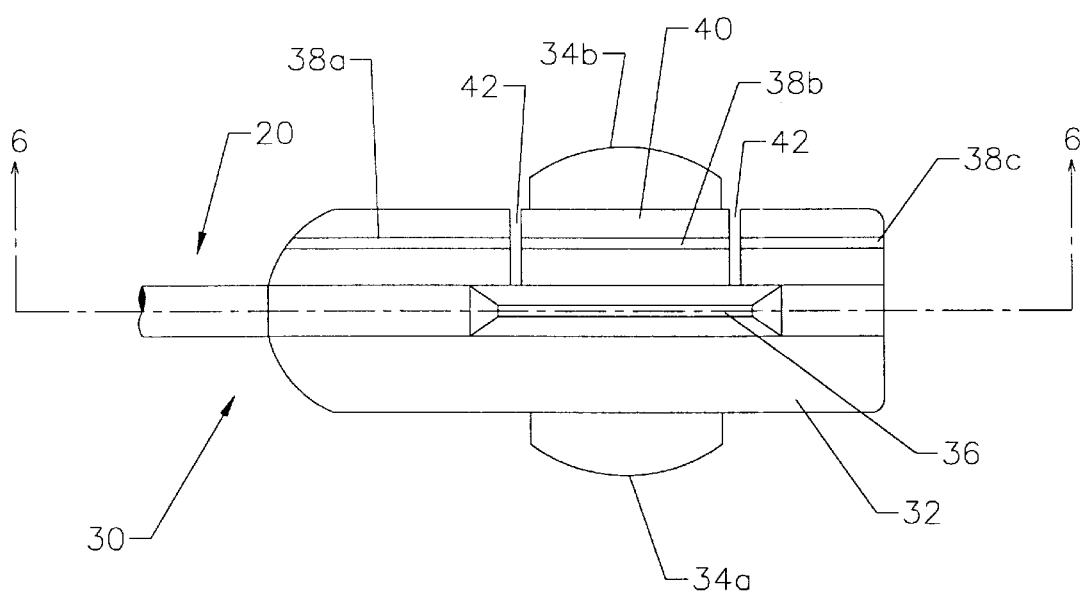
FIG. 4 is an enlarged top view of the clamp portion of the introducer of FIG. 1.
Figure 5:
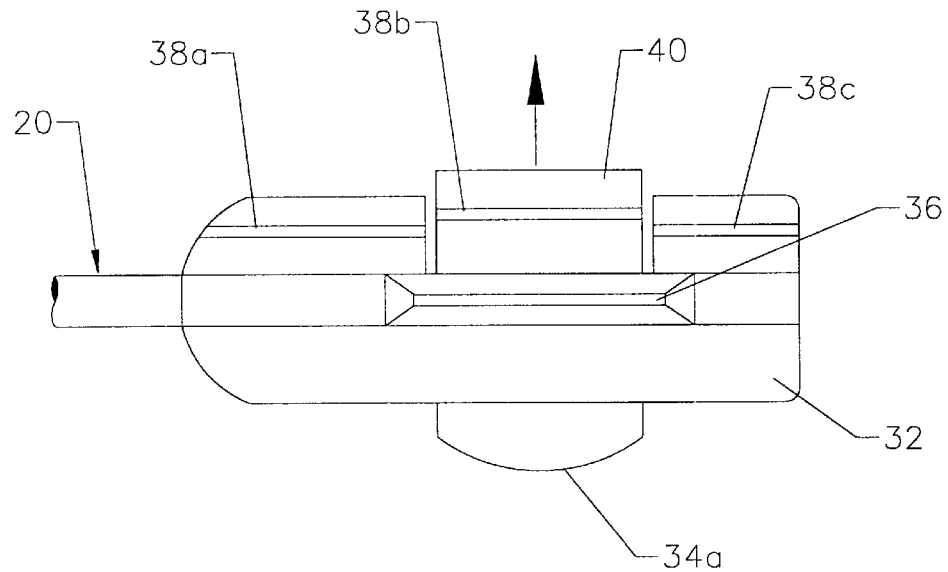
FIG. 5 is an enlarged top view of the clamp portion as seen in FIG. 4 with the guidewire channel in the guidewire clamping position.

FIGS. 1 and 2 are perspective views of one illustrative introducer 10 according to the present invention. The introducer 10 includes a tubular body 20 and a clamp 30 attached to the proximal end 22 of the tubular body 10. The tubular body 10 includes a lumen extending from the proximal end 22 to the distal end 24 of the body 20. Also included in the body 20 is an opening or port 26 in the sidewall of the body 20. As will be described in more detail below, the opening 26 is provided to allow a guidewire (not shown) to exit the tubular body 20 before the clamp 30.

The tubular body also preferably includes a slot 28 extending from the proximal end 22 to the distal end 24 of the body 20. The slot 28 extends through the opening 26 as seen in FIGS. 1 and 2 and allows for removal of the tubular body 20 of the introducer 10 from a stent delivery catheter as discussed more completely below. In addition, a portion 29 of the tubular body 20 is preferably cut-away at the point where the tubular body 20 is joined to the clamp 30 to prevent the tubular body 20 from interfering with the proper operation of the clamp 30.

In preferred embodiments, the distance from the opening 26 to the distal end 24 of the tubular body 20 is sufficient to contain a stent located on a delivery catheter (before deployment). As a result, the introducer 10 can also be used to protect a stent located on a delivery catheter before the stent is deployed within a guiding catheter.

It is preferred that the tubular body 20 be generally flexible but also posses sufficient stiffness in the axial direction, i.e., along the length of the body 20, to facilitate insertion of the distal end 24 of the body 20 into the proximal end of a guiding catheter as will be described in more detail below. The illustrated clamp 30 is preferably formed by injection molding, although any suitable method of manufacturing the clamp portion of the introducer 10 is contemplated, such as insert injection molding, machining, etc. If the clamp 30 is manufactured using injection molding of a single material, one preferred material is Polyethylene (PE).

The connection between the body 20 and the clamp 30 can be effectuated by any suitable technique including adhesive bonding, welding, mechanical attachment (hooks, etc.). Regardless of the actual technique or techniques used to connect the body 20 and clamp 30, it is preferred that the body 20 and the clamp 30 be inseparable during normal use of the introducer 10.

One preferred clamp 30 is illustrated in FIGS. 1 and 2, as well as in various other views in FIGS. 3–7. The illustrated clamp 30 includes a barrel 32 from which two levers 34a and 34b extend. For simplicity, the levers 34a and 34b will be referred to as levers 34 below. The barrel 32 also includes a catheter shaft channel 36 and a guidewire channel 38 that is provided in three sections 38a, 38b and 38c. The guidewire channel 38 is preferably wide enough to receive a guidewire over which a stent delivery catheter is advanced during stent deployment.

Figure 6:
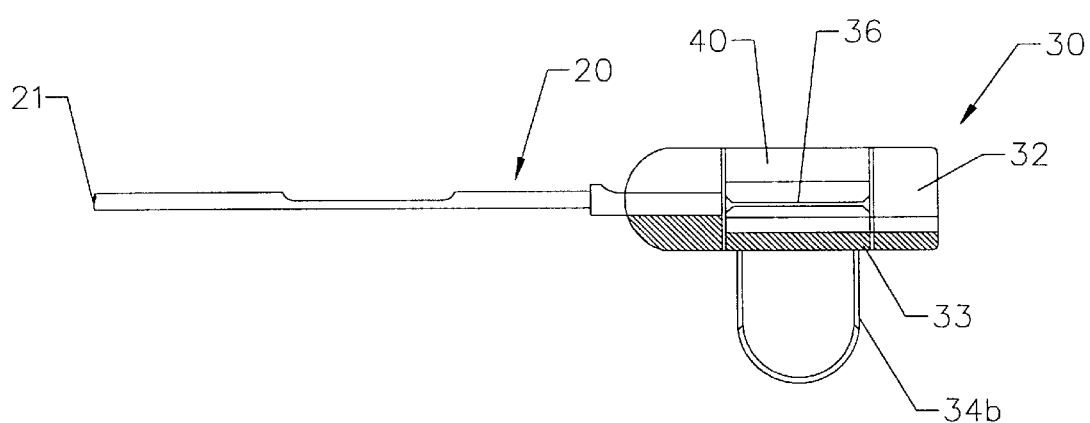
FIG. 6 is a cross-sectional view of the clamp taken along line 6—6 in FIG. 4.

The catheter shaft channel 36 is bounded on one side by a movable clamp member 40 that is resiliently connected to the remainder of the clamp barrel 32 along the bottom 33 of the barrel 32 (see FIG. 6). As a result, squeezing the levers 34 together causes the clamp member 40 to rotate about an axis extending through the resilient bottom 33 of the barrel 32. As the clamp member 40 rotates about the bottom 33 of the barrel 32, the width of the catheter shaft channel 36 changes.

The catheter shaft channel 36 is preferably in coaxial alignment with the lumen 21 of the tubular body 20 (see FIG. 6). As a result, a catheter shaft (not shown) can extend through the catheter shaft channel 36 and into the lumen 21 of the tubular body 20 without any significant bends or changes in direction.

The clamp member 40 is defined by slots 42 formed in the clamp barrel 32. The slots 42 allow the clamp member 40 to move relative to the remainder of the clamp barrel 32. They also separate the guidewire channel 38 into three separate sections 38a, 38b and 38c. As the clamp member 40 is moved outwardly from the catheter shaft channel 36, the central section 38b of the guidewire channel 38 is moved out of alignment with the sections 38a and 38c on each end of the clamp barrel 32. As a result, any guidewire contained in the guidewire channel 38 is prevented from moving within the channel 38 by friction as the guidewire is slightly deformed.

The clamp barrel 32 also preferably includes a void 35 located between the catheter shaft channel 36 and the resilient bottom 33 of the barrel 32. The void 35 also helps to decrease the stiffness of the barrel 32, allowing easier opening of the catheter shaft channel 36 using the levers 34. In addition, the void 35 also moves the axis about which the clamp member 40 rotates during movement away from the catheter shaft channel 36, thereby increasing the width to which the catheter shaft channel 36 can be opened.

Operation of the clamp 30 is illustrated in FIGS. 8 and 9. It is preferred that the clamp 30 be biased such that the catheter shaft channel 36 is at a width (referred to herein as the clamping width) that clamps the shaft 52 of a stent delivery catheter firmly enough to prevent movement of the clamp 30 relative to the shaft 52. The movement is typically prevented by frictional forces between the catheter shaft channel 36 and the shaft 52.

With the shaft 52 of a stent delivery catheter located within the catheter shaft channel 36 and a guidewire 60 located within the guidewire channel 38, the guidewire 60 can be clamped within the guidewire channel 38 by lightly squeezing the levers 34. That same squeezing action used to clamp the guidewire 60 within the guidewire channel 38 simultaneously increases the width of the catheter shaft channel 36 as the clamp member 40 rotates about the resilient bottom 33 of the barrel 32. With the proper pressure, the catheter shaft channel 36 can be increased from the clamping width at which the shaft 52 of the stent delivery catheter is retained within the catheter shaft channel 36 to an advancing width at which the shaft 52 of the stent delivery catheter can be advanced through the catheter shaft channel 36 (while the guidewire 60 remains fixed within the guidewire channel 38).

The guidewire 60 within the guidewire channel 38 will typically prevent the catheter shaft channel 36 from opening far enough to allow the shaft 52 of the stent delivery catheter to lift out of the catheter shaft channel 36. The guidewire does so by limiting the movement of the clamping member 40 relative to the remainder of the clamp barrel 32 because the guidewire will tolerate only a limited amount of deformation as the section 38b of the guidewire channel 38 is moved out of alignment with the sections 38a and 38c.

FIG. 9 illustrate removal of the clamp 30 from the shaft 52 of the stent delivery catheter. As discussed above, removal of the shaft 52 from the catheter shaft channel 36 is preferably accomplished only after a guidewire has been removed from the guidewire channel 38. After the guidewire channel 38 is clear, the levers 34 can be squeezed to increase the width of the catheter shaft channel 36 to a point at which the shaft 52 of a stent delivery catheter can be lifted out of the catheter shaft channel 36. After the shaft 52 of the stent delivery catheter is out of the clamp 30, the introducer 10 is removed from the stent delivery catheter by pulling the shaft 52 through the slot 28 formed along the length of the tubular body 20, thereby completing removal of the introducer 10 from the stent delivery catheter.

Figure 10:
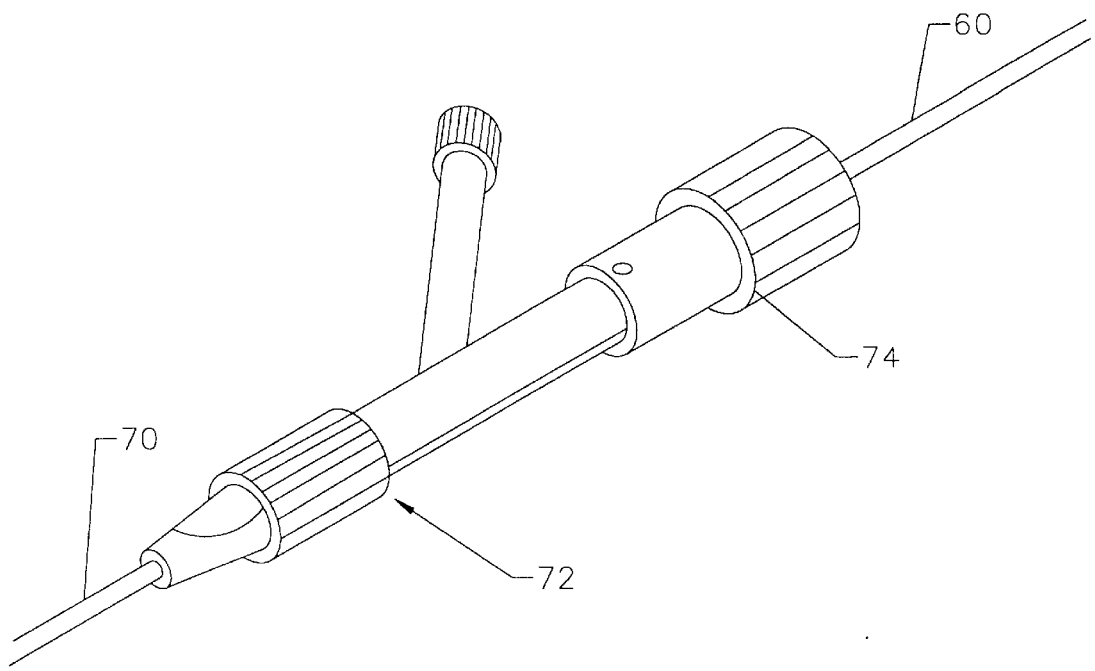
FIG. 10 is a perspective -view of a guiding catheter terminating in y-connector and a guidewire in place within the guiding catheter.

FIGS. 10–13 illustrate one method of using the introducer 10 in connection with a stent delivery catheter 50 to be introduced over a guidewire 60 through a guiding catheter 70 including a y-connector 72. FIG. 10 illustrates the guiding catheter 70 with a y-connector 72 located at its proximal end 74. A guidewire 60 is depicted as extending though the y-connector 72. The guidewire 60 is preferably clamped in position by the valve 74 located at the proximal end of the y-connector 72.

Figure 11:
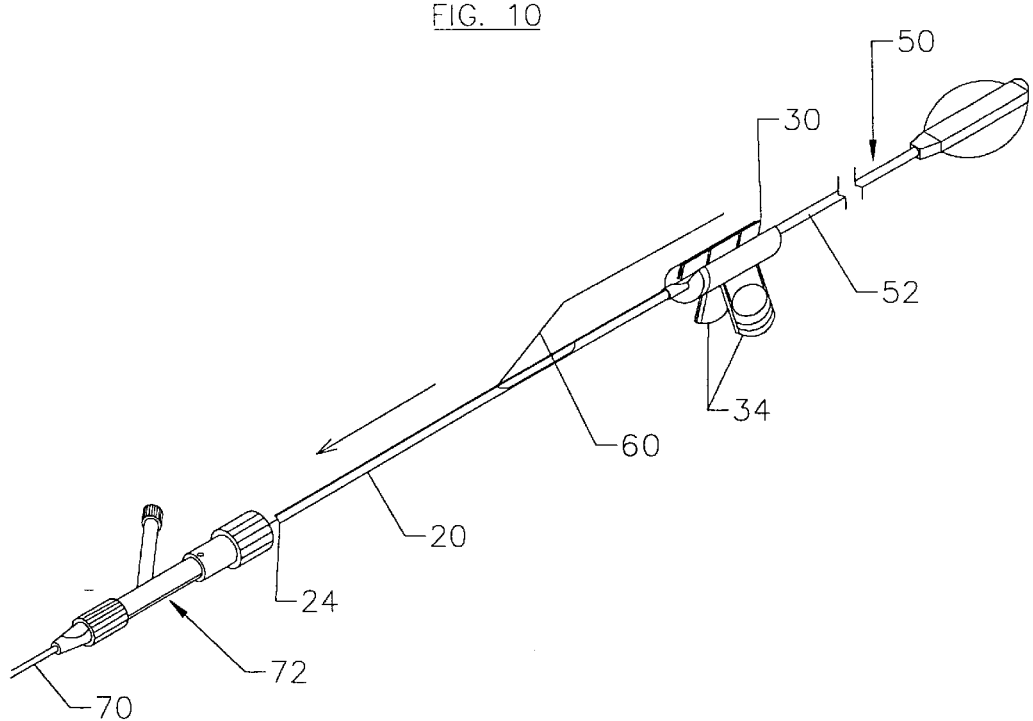
FIG. 11 is a perspective view of an introducer according to the present invention with a stent delivery catheter located therein after the guidewire has been threaded through the stent delivery catheter and tubular body portion of the introducer.
Figure 12:
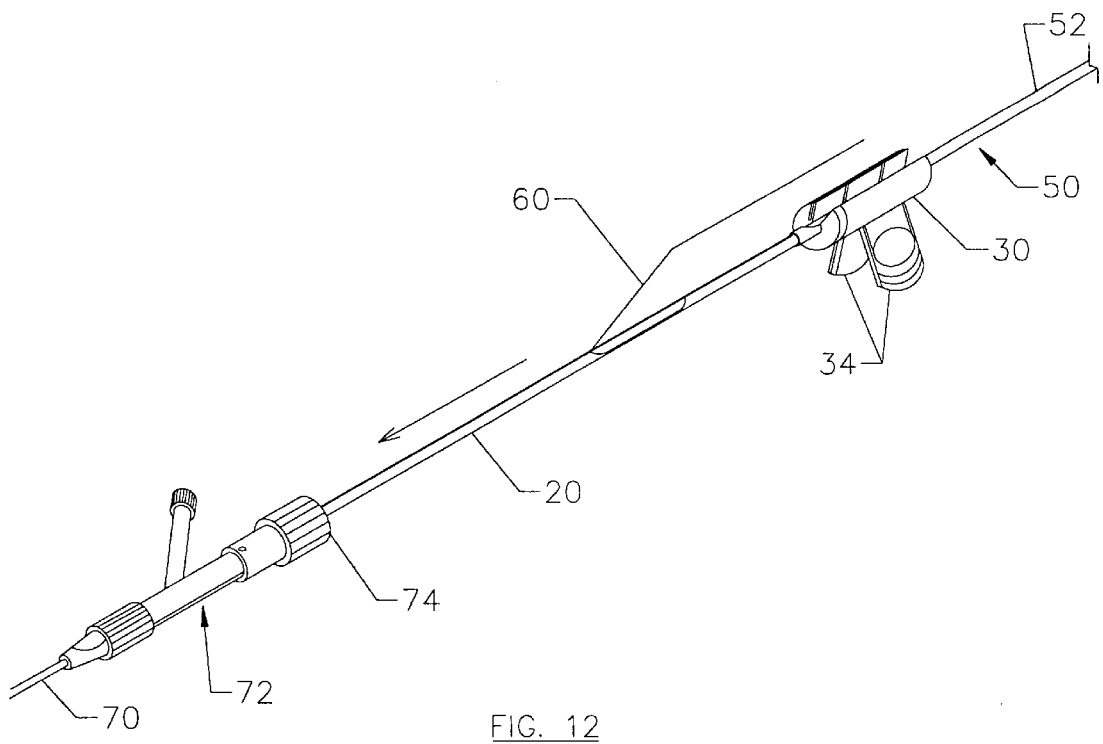
FIG. 12 is a perspective view of the introducer and stent delivery catheter of FIG. 11 after the distal end of the introducer is inserted into the y-connector of the guiding catheter.

FIG. 11 illustrates the guidewire 60 as threaded though the distal end 24 of the tubular body 20 of the introducer 10. Although not explicitly illustrated, it will be understood that the guidewire 60 is also threaded through a guidewire lumen in the stent delivery catheter 50. The guidewire exits the stent delivery catheter 50 through a suitable port located therein (not shown) and also exits the tubular body 20 of the introducer 10 through the port 26. One advantage of the introducer 10 can be seen with reference to FIG. 11 where, because of the clamping force of the clamp 30 on the shaft 52 of the stent delivery catheter 50, the tubular body 20 of the introducer 10 need not be squeezed during threading of the guidewire 60 through the distal portion of the stent delivery catheter 50. As a result, the stent located on the stent delivery catheter 50 is not susceptible to damage from mishandling during this phase of the procedure (as are some stents in conventional delivery procedures).

With the guidewire 60 properly threaded through the stent delivery catheter 50 and introducer 10, the stent delivery catheter 50 and introducer 10 can be advanced into the valve 74 at the proximal end of the y-connector 50 a illustrated in FIG. 10. Because the stent delivery catheter 50 is firmly located within the clamp 30, the user need not handle the distal portion of the introducer 50 directly and can, instead, hold the clamp 30 during advancement, thereby reducing the risk of damage to the stent located at the distal end of the stent delivery catheter 50.

Figure 13:
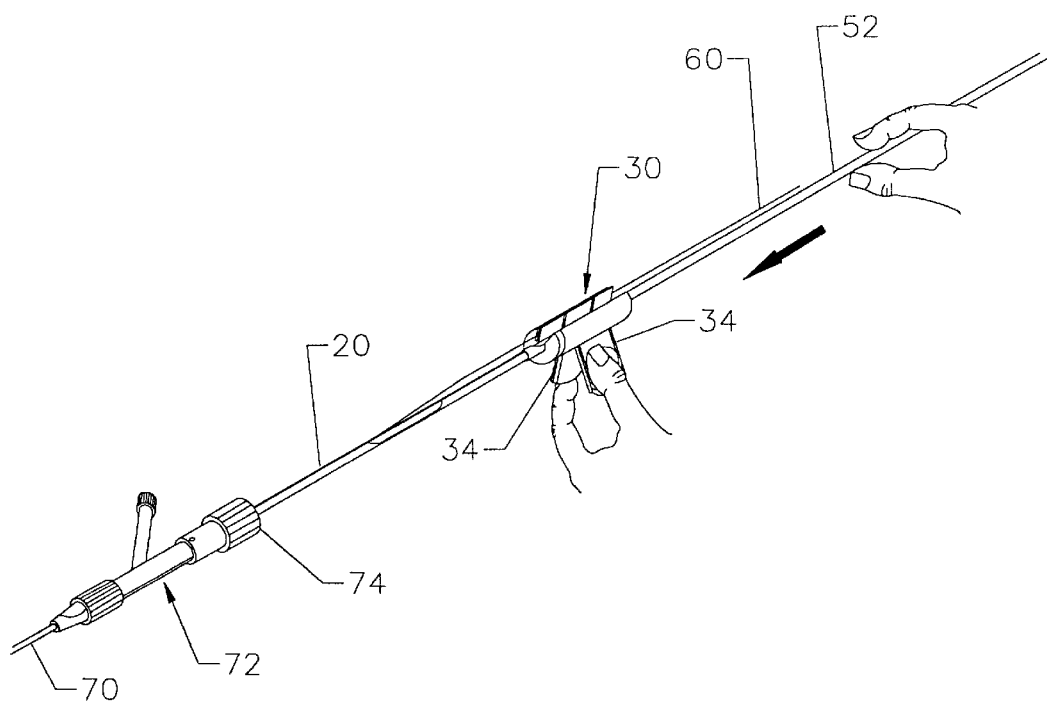
FIG. 13 is a perspective view of the introducer of FIG. 12 during advancement of the stent delivery catheter through the guiding catheter while clamping the guidewire with the introducer.

With the distal end 24 of the introducer 10 in location, the guidewire 60 is preferably placed within the guidewire channel 38 of the clamp 30 of the introducer 10 as illustrated in FIG. 13. The levers 34 on the clamp 30 are then squeezed to accomplish two operations simultaneously. As discussed in connection with the cross-sectional view of FIG. 6, squeezing the levers 34 with a guidewire 60 located in the guidewire channel 38 clamps the guidewire 60 firmly within the guidewire channel 38 while releasing the shaft 52 of the stent delivery catheter 50 for sliding movement through the clamp 30. The result is that the guidewire 60 can be retained in its proper position while the stent on the stent delivery catheter 50 is advanced through the guiding catheter 70 to the stenotic region at which it will be deployed. One advantage of this procedure is illustrated in FIG. 13 where a single user can accomplish all of the these operations without assistance.

After the stent on the stent delivery catheter 50 is in position, the introducer 10 can be removed from the stent delivery catheter 50 by first removing the guidewire 60 from the guidewire channel 38 in clamp 30. With the guidewire 60 removed from channel 38, the user can hold the guidewire 60 and stent delivery catheter 50 in one hand and squeeze the levers 34 on the clamp 30 with the other hand to open the catheter shaft channel 36 of the clamp 30 (see FIG. 9). The clamp 30 can then be pulled away from the shaft 52 of the stent delivery catheter 50. Further separation of the clamp 30 and shaft 52 will result in removal of the shaft 52 from the tubular body 20 of the introducer 10 through the slot 28.

The preceding specific embodiments are illustrative of the practice of the invention. It is to be understood, however, that other expedients known to those skilled in the art or disclosed herein, may be employed without departing from the scope of the appended claims.

No. Component
10 Introducer
20 Tubular Body
22 Proximal End of Tubular Body
24 Distal End of Tubular Body
26 Port in Tubular Body
28 Slot in Tubular Body
29 Cut-Away Portion of Tubular Body
30 Clamp
32 Clamp Barrel
34a/34b Clamp Levers
35 Clamp Barrel Void
36 Catheter Shaft Channel
38/38a/38b/38c Guidewire Channel
40 Clamping Member
42 Slots in Clamp Barrel
52 Stent Delivery Catheter Shaft
60 Guidewire
70 Guiding Catheter
72 Y-Connector
74 Valve

What is claimed is:

1. An introducer for introducing a catheter into a stent delivery system, the introducer comprising:
    a generally tubular body having a proximal end and a distal end, the body comprising a lumen formed by a sidewall and an opening in the sidewall between the proximal and distal ends;
    a clamp attached to the proximal end of the body, the clamp comprising a catheter shaft channel in coaxial alignment with the tubular body lumen, the catheter shaft channel movable between a clamping width and an advancing width that is larger than the clamping width; and
    a guidewire channel offset from the catheter shaft channel, the guidewire channel capable of receiving and retaining a guidewire in a fixed position relative to the clamp.

2. An introducer according to claim 1, wherein the catheter shaft channel is biased in the clamping width.

3. An introducer according to claim 1, wherein the clamp further comprises a movable clamp member located on one side of the catheter shaft channel.

4. An introducer according to claim 3, wherein the guidewire channel is located in the movable clamp member.

5. An introducer according to claim 3, wherein the movable clamp member rotates about an axis of rotation when the catheter shaft channel is moved from the clamping width to the advancing width.

6. An introducer according to claim 5, further comprising a first lever operatively attached to the movable clamp member and a second lever fixedly attached to the clamp, whereby rotation of the first lever about the axis of rotation rotates the movable clamp member about the axis of rotation.

7. An introducer according to claim 1, wherein the catheter shaft channel defines a catheter shaft channel axis and the guidewire channel defines a guidewire channel axis, and further wherein the catheter shaft channel axis and the guidewire channel axis are offset from and generally aligned with each other.

8. An introducer according to claim 1, wherein the lumen in the tubular body has a length between the opening and the distal end sufficient to receive a stent therein.

9. An introducer for introducing a catheter into a stent delivery system, the introducer comprising:
    a generally tubular body having a proximal end and a distal end, the body comprising a lumen formed by a sidewall and an opening in the sidewall between the proximal and distal ends;
    a clamp attached to the proximal end of the body, the clamp comprising a movable clamp member located on one side of a catheter shaft channel that is in coaxial alignment with the lumen of the tubular body, wherein the movable clamp member rotates about an axis of rotation to move the catheter shaft channel from a clamping width to an advancing width that is larger than the clamping width, and further wherein the movable clamp member is biased to maintain the catheter shaft channel in the clamping width; and
    a guidewire channel offset from the catheter shaft channel, the guidewire channel capable of receiving and retaining a guidewire in a fixed position relative to the clamp.

10. A combination comprising:
    a catheter comprising a shaft with proximal and distal ends;
    a stent located proximate the distal end of the shaft of the catheter;
    an introducer comprising:
        a generally tubular body having a proximal end and a distal end, the body comprising a lumen formed by a sidewall and an opening in the sidewall between the proximal and distal ends; wherein the stent and a portion of the shaft of the catheter are located within the lumen between the opening and the distal end of the tubular body;
        a clamp attached to the proximal end of the body, the clamp comprising a catheter shaft channel in coaxial alignment with the tubular body lumen, the catheter shaft channel movable between a clamping width and an advancing width that is larger than the clamping width, wherein the shaft of the catheter is located within the catheter shaft channel; and a guidewire channel offset from the catheter shaft channel, the guidewire channel capable of receiving and retaining a guidewire in a fixed position relative to the clamp.

11. A combination according to claim 10, wherein the catheter shaft channel is biased in the clamping width.

12. A combination according to claim 10, wherein the clamp further comprises a movable clamp member located on one side of the catheter shaft channel.

13. A combination according to claim 12, wherein the guidewire channel is located in the movable clamp member.

14. A combination according to claim 12, wherein the movable clamp member rotates about an axis of rotation when the catheter shaft channel is moved from the clamping width to the advancing width.

15. A combination according to claim 14, further comprising a first lever operatively attached to the movable clamp member and a second lever fixedly attached to the clamp, whereby rotation of the first lever about the axis of rotation rotates the movable clamp member about the axis of rotation.

16. A combination according to claim 10, wherein the catheter shaft channel defines a catheter shaft channel axis and the guidewire channel defines a guidewire channel axis, and further wherein the catheter shaft channel axis and the guidewire channel axis are offset from and generally aligned with each other.

17. A method of introducing a stent in a catheter based stent delivery system comprising:

providing a combination comprising a catheter comprising a shaft with a proximal end, a distal end and a guidewire lumen; a stent located proximate the distal end of the shaft of the catheter; and an introducer comprising:

a generally tubular body having a proximal end and a distal end, the body comprising a lumen formed by a sidewall and an opening in the sidewall between the proximal and distal ends; wherein the stent and a portion of the shaft of the catheter are located within the lumen between the opening and the distal end of the tubular body;

a clamp attached to the proximal end of the body, the clamp comprising a catheter shaft channel in coaxial alignment with the tubular body lumen, wherein the shaft of the catheter is located within the catheter shaft channel; and a guidewire channel offset from the catheter shaft channel;

inserting a guidewire into the guidewire lumen of the catheter, the guidewire passing into the distal end of the tubular body of the introducer and through the opening in the sidewall of the tubular body;

advancing the distal end of the tubular body of the introducer along the guidewire to a guiding catheter;

simultaneously increasing the width of the catheter shaft channel from a clamping width to an advancing width and retaining the guidewire within the guidewire channel; and advancing the catheter relative to the guidewire while maintaining the catheter shaft channel at the advancing width.

* * * * *